United States Patent [19]

Tipp

[11] Patent Number: 5,419,346
[45] Date of Patent: May 30, 1995

[54] INTERDENTAL TOOTHPICK AND STIMULATOR TOOL

[76] Inventor: Raymond P. Tipp, P.O. Box 3778, Missoula, Mont. 59806

[21] Appl. No.: 224,308

[22] Filed: Apr. 7, 1994

[51] Int. Cl.⁶ .............................................. A61C 15/02
[52] U.S. Cl. ..................................... 132/329; 132/321
[58] Field of Search ............... 132/321, 322, 329, 328; 433/141, 144

[56] References Cited

U.S. PATENT DOCUMENTS

| | | | |
|---|---|---|---|
| D. 249,062 | 8/1978 | Crafoord | 433/141 |
| 1,220,933 | 3/1917 | Bates | 433/143 |
| 1,385,288 | 7/1921 | Walker | 132/328 |
| 1,503,610 | 8/1924 | Smith | 433/143 |
| 1,527,028 | 2/1925 | Daniel | 132/321 |
| 1,663,826 | 3/1928 | Bier | 433/141 |
| 1,679,651 | 8/1928 | Crowell | 132/328 |
| 3,672,378 | 6/1972 | Silverman | 132/329 |
| 4,110,908 | 9/1978 | Cranston | 433/143 |
| 4,326,548 | 4/1982 | Wagner | 132/328 |
| 4,643,676 | 2/1987 | Jansheski | 433/143 |
| 4,759,713 | 7/1988 | Heiss et al. | 433/141 |
| 5,076,301 | 12/1991 | Sulskis | 132/321 |
| 5,090,907 | 2/1992 | Hewitt et al. | 433/141 |
| 5,125,424 | 6/1992 | Eisen | 132/328 |
| 5,127,833 | 7/1992 | Kline | 433/141 |

*Primary Examiner*—Paul Hirsh
*Attorney, Agent, or Firm*—Harry M. Cross, Jr.

[57] ABSTRACT

A dental instrument comprises an angular-fashioned metal pick 12 secured to a solid rectangular or square handle and projects from one end thereof. The pick is shaped in an angular configuration, with its stem embedded into the handle, then extended outward along the longitudinal axis of the handle. The stem is bent to provide a section that extends at an acute angle from the longitudinal axis outward to an essentially straight section. The straight section forms a transition section to a probe section. The probe section extends in a spiral curved from the end of the straight section to a blunt distal end. The probe projects forwardly on the order of approximately 8 mm or more to a tapered distal end of the probe.

4 Claims, 3 Drawing Sheets

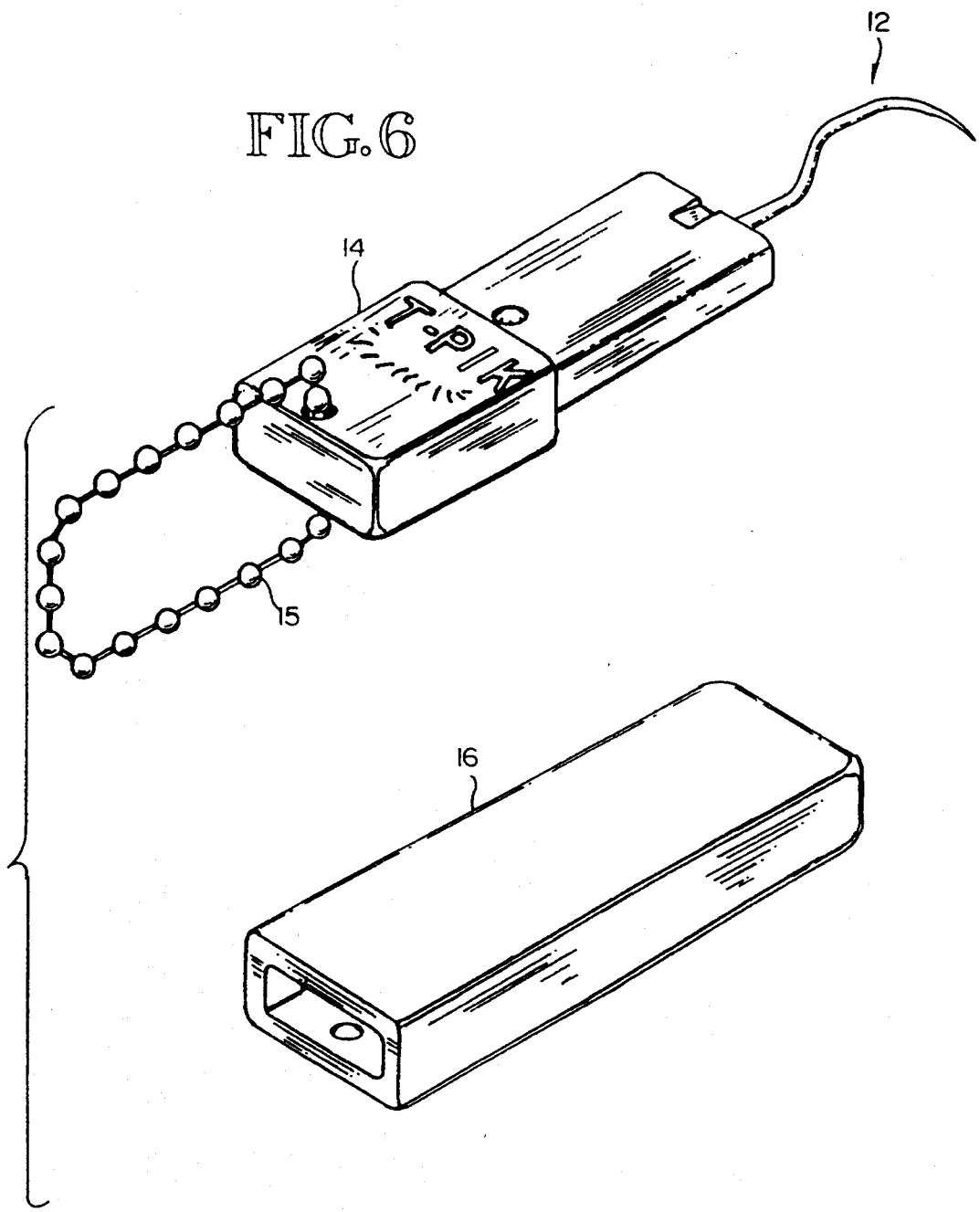

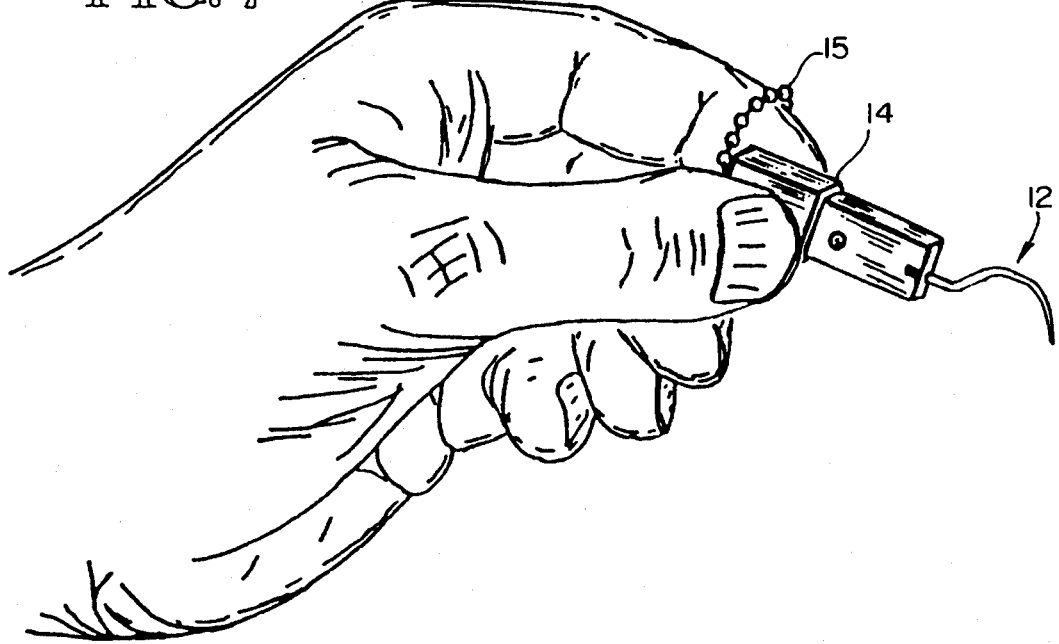

INTERDENTAL TOOTHPICK AND STIMULATOR TOOL

BACKGROUND OF THE INVENTION

1. Field of the Invention

This invention relates to oral hygiene instruments and more particularly to reusable devices for removing particles of food from spaces between the teeth and for removing soft plaque from the surfaces of the teeth.

2. Brief Description of the Prior Art

Dental tools in the form of dental picks have been proposed in the past for use in cleaning food particles from between a user's teeth. These devices, however, have been designed to function in a manner similar to a toothpick and have not been designed for use to stimulate tissue between the teeth.

From the foregoing summary, it will be appreciated that it is an object of the present invention to provide a personal toothpick and interdental stimulator of the general character described which is not subject to the disadvantage aforementioned.

A further object of the present invention is to provide a simple, compact, and efficient personal toothpick and interdental stimulator of the general character described which can be available to anyone and by them inconspicuously carried, be discreetly used wherever needed, and enable the user to dexterously manipulate the probe.

Another object of the present invention is to provide a personal toothpick and interdental stimulator of the general character described which is well suited for the safe, easy, and efficient removal of impacted food particles and material between all teeth, interproximal spaces, pockets, and various traps formed by dental and orthodontic appliances of the user's mouth, for the removal of soft plaque and for massage of the user's gums.

Another object of the present invention is to provide a personal toothpick and interdental stimulator of the general character described which, due to the long shaft of the probe, is efficient to provide a long, smooth, round surface, together with the same being manipulated in a massaging action, to massage and stimulate the user's gums.

Another object to the present invention is to provide a personal toothpick and interdental stimulator of the general character describe which, due to the long shaft of the probe, is efficient to provide a long, smooth, round surface, together with the same being manipulated in a massaging action, to massage and stimulate the user's gums as an alternative to flossing.

Yet another object of the present invention is to provide a personal toothpick and interdental stimulator of the general character described which is efficient, low in cost, suitable for economic mass production fabrication, be possessed of a high degree of resilience, and will be adapted to withstand, for an indefinite period, the usage to which toothpicks and interdental simulators are ordinarily subjected.

A further object of the present invention is to provide a personal toothpick and interdental stimulator of the general character describe which, due to its simple, compact, and rugged fabrication and design, can be conveniently and inconspicuously carried on the person, in the user's pocket, in a purse, or from a key chain with safety.

Further object of the present invention in part will be obvious and in part will be pointed out hereinafter.

With these ends in view, the invention finds embodiment in certain combinations of elements and arrangements of parts and series of steps by which the said objects and certain other objects are attained, all as more fully described with reference to the accompanying drawings and the scope of which is more particularly pointed out and indicated in the appended claims.

SUMMARY OF THE INVENTION

The invention comprises a portable, combination, personal toothpick and interdental stimulator, which includes a long tapered resilient metal probe shaft off the stem which is formed and fashioned for easy, safe, comfortable, and convenient removal of impacted food particles and material from between teeth, interproximal spaces, and dental appliances in the user's mouth without interference with the buccal areas of the mouth. The distal end of the stem may be seated within one end of a rectangle or square shaped handle which is formed on the opposite end with knurled or serrated surfaces and a hole. A sheath formed complementary to the shape of the pick and handle covers the pick and end of the handle when the pick is not in use and when being carried in a pocket, purse, or on a chain or cord. The sheath includes a protrusion which corresponds with a depression in the handle to form a latch lock to secure the handle within the case.

The probe shaft is tapered to a relatively small diameter with a blunt end sufficient to enter the interproximal spaces, pockets, and various traps formed by bridgework, orthodontic appliances, and the like. The probe shaft can be employed to massage the gums as an interdental stimulator and the probe end to remove soft plaque.

The shape, form, and size of the pick and sheath allows the user to comfortably, conveniently, and inconspicuously carry the pick in a pocket, purse, or from a key chain, cord or holder with safety until the need for its use arises, when it will be readily available.

In summary, then the present invention comprises a personal toothpick and interdental stimulator instrument comprising handle means adapted to be gripped between a user's thumb and forefinger, and pick means extending outward from the handle means along a longitudinal axis of the handle means for insertion into the user's mouth. The pick means comprises a stainless elongated metal member having a first straight section longitudinally extending from the handle means, a second section extending from the first section and angled outwardly from the first section at an acute angle with respect to the longitudinal axis, an essentially straight third section extending from the second section, and a probe section extending from the straight third section. The straight third section is displaced from the longitudinal axis and is generally parallel thereto. The probe section is shaped in the form of a reverse spiral with its radius of curvature progressively lengthening from its point of connection with the straight third section, and has a circular cross-section and a length of at least about 8 mm, and is tapered from a larger diameter at its point of connection with the straight third section to a blunt end having a smaller diameter at its distal end.

BRIEF DESCRIPTION OF THE DRAWINGS

In the accompanying drawings in which is shown of the various possible exemplary embodiments of the invention:

FIG. 6 is a perspective view of the personal toothpick and interdental stimulator; and FIG. 7 is a perspective view of the personal toothpick and interdental stimulator being held in a user's hand preparatory to its use.

Similar numerals of reference designate corresponding parts in all view of the drawings.

DESCRIPTION OF THE PREFERRED EMBODIMENT

Figure 1:
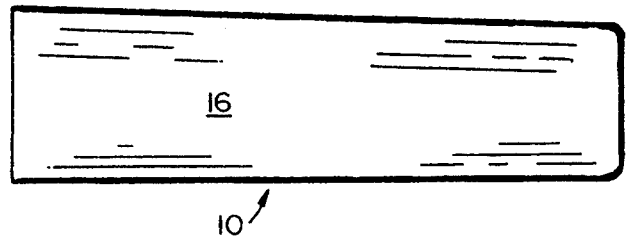
FIG. 1 is a side view in elevation of the sheath portion of the personal toothpick and interdental stimulator.

Referring now in detail to the drawings, the references numeral 10 denotes generally a dental instrument constructed with, and embodying the invention. The instrument 10 comprises an angular-fashioned metal pick 12 employed for the removal of impacted food and material between teeth, interproximal spaces, pockets and various traps formed by dental and orthodontic appliances, and as an interdental stimulator. The stem 24 of the pick 12 is secured to a solid rectangular or square handle 14 and projects from one end thereof. The pick end of the handle 14 has at least one latch lock depression 26 (two being shown) and is selectively covered by a sheath 16 which contains the corresponding male flange 18 of the latch lock. The opposite end of the handle embodies a hole 32 and finger grip depressions 30.

Figure 4:
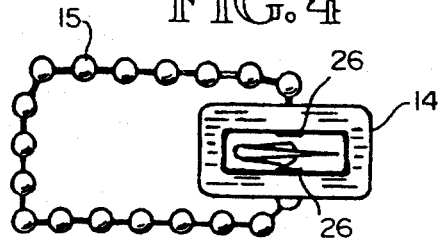
FIG. 4 is an end view of the probe end of the FIG. 2 handle and probe portion.
Figure 5:
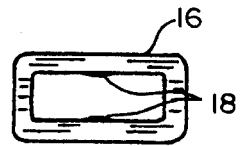
FIG. 5 is an end view of the opening into the FIG. 1 sheath portion.

In accordance with the present invention, the toothpick-stimulator/probe, due to its simple, compact, and rugged fabrication and design, may be conveniently, inconspicuously, comfortably, and efficiently carried about the person, in the user's pocket, in a purse or similar case, or suspended from a key chain or cord. For this purpose, the handle 14 is of solid construction, formed rectangular or square (see FIG. 4), with a hole 32 formed to accommodate a finger security chain or cord and the surface is depressed at 30 for tactile grip and control. The opposite end of the handle 14 is smooth, has embedded therein the pick stem 24, and contains the corresponding depressions 26 of the flange 18 of the case 16 for the latch lock. When the instrument is not in use, the case 16 is positioned over the pick 12 and handle 14 to the extent that the latch lock depression 26 and flange 18 are engaged and protects the pick 12 when the toothpick-stimulator/probe is carried in the user's pocket, purse, or suspended on a chain or cord.

Figure 2:
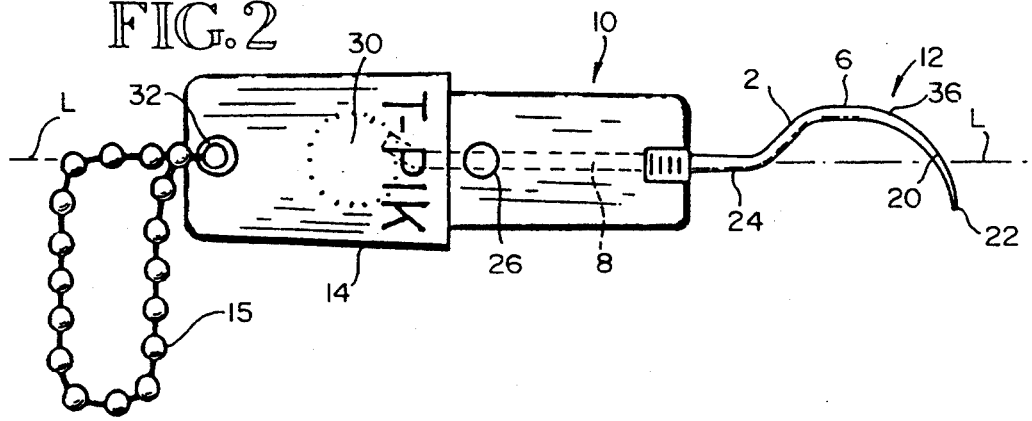
FIG. 2 is a side view in elevation of the handle and probe portion of the personal toothpick and interdental stimulator
Figure 3:
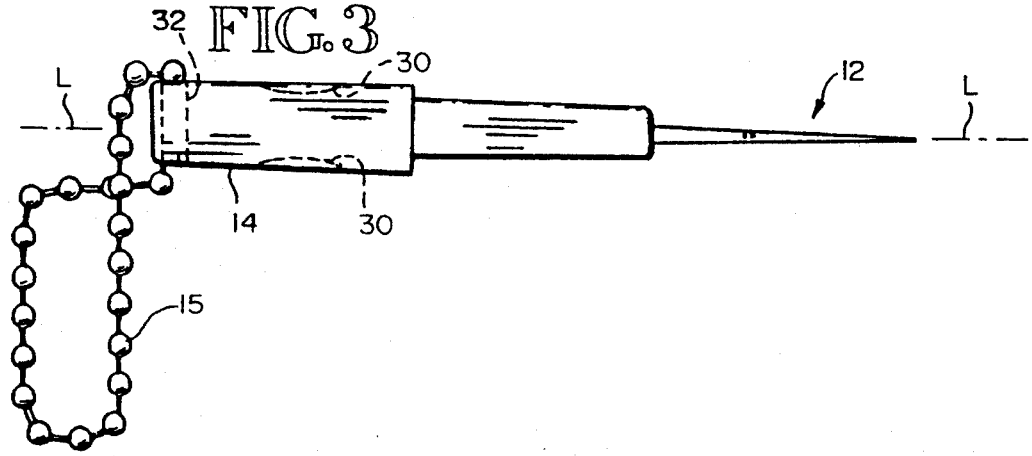
FIG. 3 is a top plan view of the FIG. 2 handle and probe portion.

Referring now to FIG. 2, wherein the pick 12 is illustrated, it will be seen that the outer segment of the pick is shaped in an angular configuration. The stem 24 has an elongated straight section 8 that is embedded into the solid handle 14 and extended outward along the longitudinal axis L of the handle 14. The stem 24 is bent to provide a section 2 that extends at an acute angle of about 45° from the longitudinal axis L outward to a straight section 6. The straight section 6 forms a transition section between section 2 and the probe section 20 and extends generally parallel to the longitudinal axis L. Straight section 6 terminates at point 36 and provides a straight transition zone. The probe section commences at point 36 and is shaped in the form of a reverse spiral curve that progressively opens as it extends from point 36 to its tip end 22. Straight section 6 is essentially linear, but may have a very slight curvature with its midpoint region being parallel to the longitudinal axis L. Probe 20 projects forwardly because its curvature progressively opens, that is its radius of curvature becomes progressively longer from point 36 to end 22. The extent of the outermost portion of probe 20 is not perpendicular to the longitudinal axis L. This forward projection is on the order of approximately 8 mm or more from point 36 to the tapered distal end 22 of the probe 20.

Probe 20, commencing at point 36, has a circular cross-section and is tapered from a diameter of about 0.0047 inches at its proximal end at point 36 to a diameter of about 0.0017 at its distal end 22. Probe 20 is ideally suited anatomically to be easily and comfortably inserted into the interproximal spaces and safely remove impacted material as well as to be employed an utilized to massage and stimulate the user's gums. The tapered blunt end 22 of probe 20 is an efficient tool to engage and dislodge soft plaque. In order for the instrument of this invention to be correct, anatomically, it is important that probe section 20 be shaped in a reverse spiral curve so that its radius of curvature progressively lengthens and that it proceeds from a straight portion 6 that is displaced from the longitudinal axis L.

The personal toothpick-stimulator/probe of the present invention is adapted for an individual's personal use which will not rust and may be readily cleaned for hygienic purposes by generally accepted means of washing or sterilization.

Thus, it will be seen that there is provided a simple, compact, efficient, and practical toothpick and interdental simulator/probe which achieves the various objects of the present invention and which is well adapted to meet the conditions of practical use. It achieves the purposes and meets the conditions of a simple and compact personal toothpick and interdental stimulator/probe which is well adapted to meet the conditions of such a dental instrument to be conveniently, comfortably, inconspicuously, and practical to carry upon the person so as to encourage users to carry the instrument with them and thereby facilitate the general availability of the instrument whenever needed.

Because various embodiments might be made of the present invention and since various changes might be made in the exemplary embodiment set forth herein, it is to be understood and appreciated that all matter depicted in the accompanying drains or described herein is to be interpreted as illustrative and not in a limiting sense.

While the preferred embodiment of the invention has been described herein, variations in the design may be made. The scope of the invention, therefore, is only to be limited by the claims appended hereto.

The embodiments of the invention in which an exclusive property is claimed are defined as follows:

In the claims:

1. A personal toothpick and interdental stimulator instrument comprising handle means adapted to be gripped between a user's thumb and forefinger, and pick means extending outward from said handle means along a longitudinal axis of said handle means for insertion into the user's mouth;

said pick means comprising a stainless elongated metal member having a first straight section longitudinally extending from said handle means, a second section extending from said first section and angled outwardly from said first section at an acute angle with respect to said longitudinal axis, an essentially straight third section extending from said second section, and a probe section means extending from said straight third section;

said straight third section being displaced from said longitudinal axis and being generally parallel thereto; and said probe section means being provided in the form of a tapered metal shaft shaped in the form of a reverse spiral with its radius of curvature progressively lengthening from its point of connection with said straight third section so that the extent of said probe section means terminates at a distal end and forms an acute angle with respect to said longitudinal axis, and having a circular cross-section and a length of at least about 8 mm, and being tapered from a larger diameter at its point of connection with said straight third section of about 0.0047 inches to a blunt end having a smaller diameter at its distal end of about 0.0017 inches so that said probe section means may be inserted between a user's tooth and gum;

said pick means, as a consequence of the configuration of said probe section means, providing a long, smooth surface, capable of being inserted between a user's tooth and gum for stimulating and massaging the user's gums as an alternative to flossing.

2. The instrument of claim 1 including a bead chain means inserted through an aperture provided therefore in the end of said handle means, said bead chain means having a length and being oriented with respect to said handle means that a user may loop said bead chain means about his index finger whereby said handle means is secured when pinched between the user's thumb and index finger so that said bead chain means provides an extension of said handle means to aid in the control and manipulation of said pick means.

3. The instrument of claim 1 including sheath means adapted to be inserted longitudinally over said pick means and secured to said handle means whereby said pick means is protected.

4. A personal toothpick and interdental stimulator instrument comprising handle means adapted to be gripped between a user's thumb and forefinger; a bead chain means inserted through an aperture provided therefore in the end of said handle means, said bead chain means having a length and being oriented with respect to said handle means that a user may loop said bead chain means about his index finger whereby said handle means is secured when pinched between the user's thumb and index finger so that said bead chain means provides an extension of said handle means to aid in the control and manipulation of a pick means; pick means extending outward from said handle means along a longitudinal axis of said handle means for insertion into the user's mouth; and sheath means adapted to be inserted longitudinally over said pick means and secured to said handle means whereby said pick means is protected said pick means comprising a stainless elongated metal member having a first section longitudinally extending from said handle means, a second section extending from said first section and angled outwardly from said first section at an acute angle with respect to said longitudinal axis, an essentially straight third section extending from said second section and a probe section means extending from said straight third section;

said straight third section being displaced from said longitudinal axis and being generally parallel thereto;

said probe section means being provided in the form of a tapered metal shaft shaped in the form of a reverse spiral with its radius of curvature progressively lengthening from its point of connection with said straight third section so that the extent of said probe section means terminates at a distal end and forms an acute angle with respect to said longitudinal axis, and having a circular cross-section and a length of at least about 8 mm, and being tapered from a larger diameter of about 0.0047 inches at its point of connection with said arcuate third section to a blunt end having a smaller diameter of about 0.0017 inches at its distal end so that said probe section means may be inserted between a user's tooth and gum;

said pick means, as a consequence of the configuration of said probe section means, providing a long, smooth surface, capable of being inserted between a user's tooth and gum for stimulating and massaging the user's gums as an alternative to flossing.

* * * * *